(12) United States Patent
Takaguchi et al.

(10) Patent No.: US 11,753,367 B2
(45) Date of Patent: Sep. 12, 2023

(54) XYLYLENE DIISOCYANATE COMPOSITION, POLYMERIZABLE COMPOSITION FOR OPTICAL MATERIAL, RESIN, MOLDED ARTICLE, OPTICAL ELEMENT, AND LENS

(71) Applicant: MITSUI CHEMICALS, INC., Tokyo (JP)

(72) Inventors: Masayuki Takaguchi, Chiba (JP); Masaru Kawaguchi, Fukuoka (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 17/999,678

(22) PCT Filed: Mar. 9, 2022

(86) PCT No.: PCT/JP2022/010364
§ 371 (c)(1),
(2) Date: Nov. 22, 2022

(87) PCT Pub. No.: WO2022/191247
PCT Pub. Date: Sep. 15, 2022

(65) Prior Publication Data
US 2023/0202971 A1 Jun. 29, 2023

(30) Foreign Application Priority Data
Mar. 10, 2021 (JP) .................... 2021-038757

(51) Int. Cl.
*C07C 265/14* (2006.01)
*C07C 265/08* (2006.01)
*G02B 1/04* (2006.01)
*C08G 18/71* (2006.01)
*C08G 18/20* (2006.01)
*C08G 18/38* (2006.01)
*C08G 18/76* (2006.01)

(52) U.S. Cl.
CPC .......... *C07C 265/14* (2013.01); *C07C 265/08* (2013.01); *C08G 18/2018* (2013.01); *C08G 18/2027* (2013.01); *C08G 18/3876* (2013.01); *C08G 18/712* (2013.01); *C08G 18/7614* (2013.01); *G02B 1/04* (2013.01)

(58) Field of Classification Search
CPC . C07C 265/14; C07C 265/08; C08G 18/2018; C08G 18/2027; C08G 18/3876; C08G 18/712; C08G 18/7614; G02B 1/04
See application file for complete search history.

(56) References Cited

U.S. PATENT DOCUMENTS

| | | |
|---|---|---|
| 3,549,504 A | 12/1970 | Adica et al. |
| 5,523,467 A | 6/1996 | Okazaki et al. |
| 10,294,198 B2 | 5/2019 | Halpaap et al. |
| 2019/0106529 A1 | 4/2019 | Kuma |
| 2019/0135737 A1 | 5/2019 | Rataboul-Leduc et al. |
| 2019/0292304 A1 | 9/2019 | Yamasaki et al. |

FOREIGN PATENT DOCUMENTS

| | | |
|---|---|---|
| CN | 109748822 A | 5/2019 |
| WO | 2017179575 A1 | 10/2017 |
| WO | 2018190290 A1 | 10/2018 |
| WO | 2022059820 A2 | 3/2022 |

*Primary Examiner* — Rabon A Sergent
(74) *Attorney, Agent, or Firm* — BUCHANAN INGERSOLL & ROONEY PC

(57) ABSTRACT

A xylylene diisocyanate, a compound represented by the following chemical formula (1), and a compound represented by the following chemical formula (2) are contained in a xylylene diisocyanate composition.

[Chemical Formula 1]

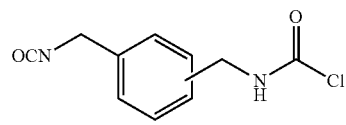

(1)

[Chemical Formula 2]

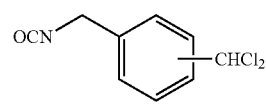

(2)

11 Claims, 1 Drawing Sheet

XYLYLENE DIISOCYANATE COMPOSITION, POLYMERIZABLE COMPOSITION FOR OPTICAL MATERIAL, RESIN, MOLDED ARTICLE, OPTICAL ELEMENT, AND LENS

TECHNICAL FIELD

The present invention relates to a xylylene diisocyanate composition, a polymerizable composition for an optical material, a resin, a molded article, an optical element, and a lens.

BACKGROUND ART

Conventionally, a xylylene diisocyanate composition as a raw material for a resin used for various industrial products has been known.

For example, a xylylene diisocyanate composition has been proposed in which a xylylene diisocyanate and a dichloromethylbenzyl isocyanate are contained and a content ratio of the dichloromethylbenzyl isocyanate is 0.6 ppm or more and 60 ppm or less (ref: for example, Patent Document 1).

CITATION LIST

Patent Document

Patent Document 1: International Patent Publication No. WO2018/190290

SUMMARY OF THE INVENTION

Problem to be Solved by the Invention

A resin produced from a xylylene diisocyanate composition may be required to have excellent heat resistance in accordance with its purpose and application. However, when the resin is produced from the xylylene diisocyanate composition described in Patent Document 1, there is a limit in improving the heat resistance of the resin.

Accordingly, the present invention provides a xylylene diisocyanate composition, a polymerizable composition for an optical material, a resin, a molded article, an optical element, and a lens capable of stably producing a resin having excellent heat resistance.

Means for Solving the Problem

The present invention [1] includes a xylylene diisocyanate composition containing a xylylene diisocyanate, a compound represented by the following chemical formula (1), and a compound represented by the following chemical formula (2).

[Chemical Formula 1]

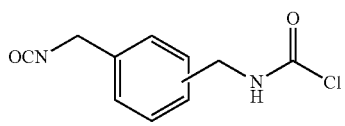

(1)

[Chemical Formula 2]

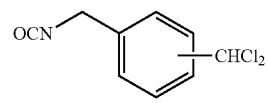

(2)

The present invention [2] includes the xylylene diisocyanate composition described in the above-described [1], wherein a mass ratio of the compound represented by the chemical formula (1) to the compound represented by the chemical formula (2) is 10000 or less.

The present invention [3] includes the xylylene diisocyanate composition described in the above-described [2], wherein a mass ratio of the compound represented by the chemical formula (1) to the compound represented by the chemical formula (2) is below 3000.

The present invention [4] includes the xylylene diisocyanate composition described in any one of the above-described [1] to [3] further including a curing catalyst represented by the following chemical formula (3), wherein a mole ratio of the curing catalyst to the compound represented by the chemical formula (1) is 2 or more.

[Chemical Formula 3]

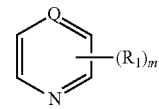

(3)

(In chemical formula (3), $R_1$ represents a straight-chain alkyl group having 1 to 20 carbon atoms, a branched alkyl group having 3 to 20 carbon atoms, a cycloalkyl group having 3 to 20 carbon atoms, or a halogen atom. "m" represents an integer of 0 to 5. When "m" is 2 to 5, the plurality of $R_1$s may be the same or different. Q represents a carbon atom or a nitrogen atom.)

The present invention [5] includes the xylylene diisocyanate composition described in the above-described [4], wherein the curing catalyst is at least one kind selected from pyridine, 3-chloropyridine, 2-methylpyridine, 3-methylpyridine, 4-methylpyridine, 2-ethylpyridine, 3-ethylpyridine, 2,6-dimethylpyridine, 3,5-dimethylpyridine, 2,4,6-trimethylpyridine, and 2-methylpyrazine.

The present invention [6] includes a polymerizable composition for an optical material including the xylylene diisocyanate composition described in any one of the above-described [1] to [5] and an active hydrogen group-containing component.

The present invention [7] includes the polymerizable composition for an optical material described in the above-described [6], wherein the active hydrogen-containing component includes at least one kind of polythiol selected from the group consisting of 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis (mercaptomethylthio)propane, 4,6-bis (mercaptomethylthio)-1,3-dithiane, 2-(2,2-bis (mercaptomethylthio)ethyl)-1,3-dithiethane, 1,1,2,2-tetrakis (mercaptomethylthio)ethane, 3-mercaptomethyl-1,5-dimercapto-2,4-dithiapentane, tris(mercaptomethylthio)methane, and ethylene glycol bis(3-mercaptopropionate).

The present invention [8] includes a resin being a cured product of the polymerizable composition for an optical material described in the above-described [6] or [7].

The present invention [9] includes a molded article including the resin described in the above-described [8].

The present invention [10] includes an optical element including the molded article described in the above-described [9].

The present invention [11] includes a lens including the optical element described in the above-described [10].

Effect of the Invention

The xylylene diisocyanate composition of the present invention contains the xylylene diisocyanate, the compound represented by the above-described chemical formula (1), and the compound represented by the above-described chemical formula (2). Therefore, the resin produced from the above-described xylylene diisocyanate composition has excellent heat resistance.

The polymerizable composition for an optical material of the present invention contains the above-described xylylene diisocyanate composition. Therefore, the resin produced from the above-described polymerizable composition for an optical material has excellent heat resistance.

The resin, the molded article, the optical element, and the lens of the present invention contain a cured product of the above-described polymerizable composition for an optical material. Therefore, the resin, the molded article, the optical element, and the lens have excellent heat resistance.

DESCRIPTION OF EMBODIMENTS

1. Xylylene Diisocyanate Composition

Figure 1:
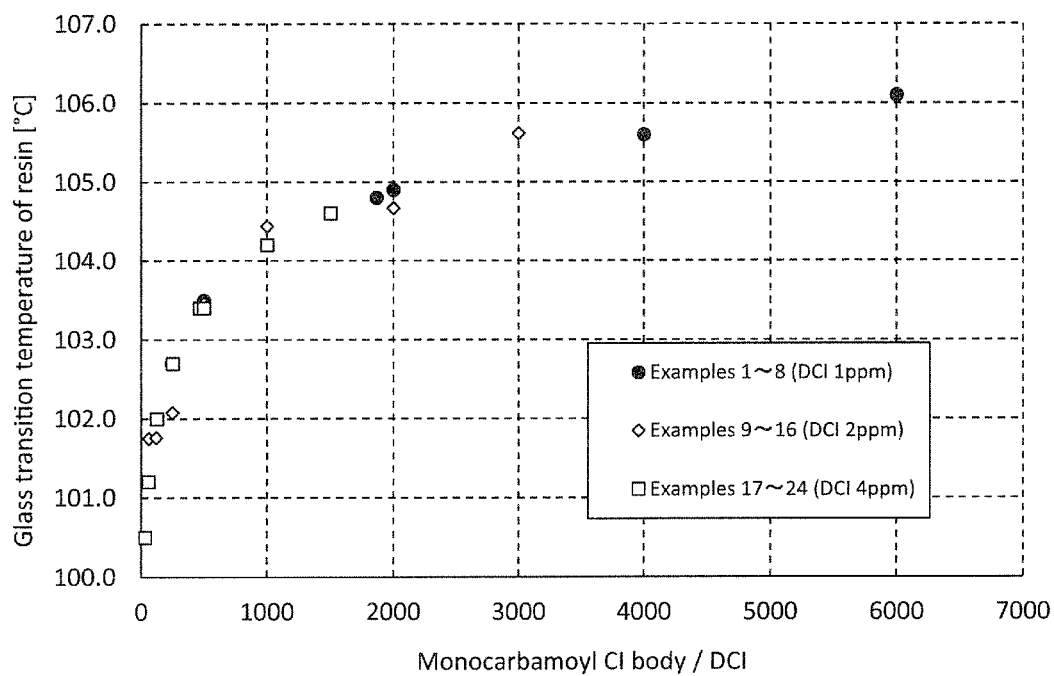
FIG. 1 shows a graph illustrating the correlation between a mass ratio of an isocyanatomethylbenzyl carbamic acid chloride to a dichloromethylbenzyl isocyanate in each xylylene diisocyanate composition of Examples and a glass transition temperature of a resin.

A xylylene diisocyanate composition of the present invention is a substantially single compound containing a xylylene diisocyanate at 98% by mass or more as a main component (that is, a xylylene diisocyanate). However, since the xylylene diisocyanate composition of the present invention contains a compound represented by the following chemical formula (1) and a compound represented by the following chemical formula (2) as secondary components, it is defined as a xylylene diisocyanate composition.

In other words, the xylylene diisocyanate composition of the present invention contains the xylylene diisocyanate, the compound represented by the following chemical formula (1), and the compound represented by the following chemical formula (2) as essential components. The xylylene diisocyanate composition may further contain a curing catalyst.

In the following, the xylylene diisocyanate composition is referred to as an XDI composition, and the xylylene diisocyanate is referred to as an XDI. Further, the compound represented by the following chemical formula (1) (isocyanatomethylbenzyl carbamic acid chloride) is referred to as a monocarbamoyl Cl body or an MCC body. Further, the compound represented by the following chemical formula (2) (dichloromethylbenzyl isocyanate) is referred to as a DCI.

[Chemical Formula 1]

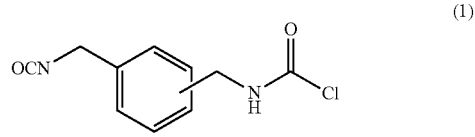

(1)

[Chemical Formula 2]

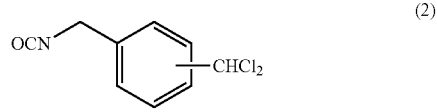

(2)

Examples of the XDI include 1,2-XDI (o-XDI), 1,3-XDI (m-XDI), and 1,4-XDI (p-XDI).

One or two or more kinds of XDIs may be contained in the XDI composition.

Of the XDIs, preferably, 1,3-XDI (m-XDI) is used.

A content ratio (purity) of the XDI is, for example, 98.00% by mass or more, preferably 99.00% by mass or more, more preferably 99.30% by mass or more, further more preferably 99.60% by mass or more, and for example, 99.95% by mass or less with respect to the total mass of the XDI composition. The content ratio of the XDI may be measured in conformity with the method described in the [0376] and [0377] paragraphs of International Patent Publication No. WO2018/190290.

The monocarbamoyl Cl body represented by the above-described chemical formula (1) is the isocyanatomethylbenzyl carbamic acid chloride, and one isocyanate group of two isocyanate groups possessed by the XDI is substituted with a carbamoyl chloride group (—NH—CO—Cl group).

Examples of the monocarbamoyl Cl body include (2-(isocyanatomethyl)benzyl)carbamic acid chloride, (3-(isocyanatomethyl)benzyl)carbamic acid chloride, and (4-(isocyanatomethyl)benzyl)carbamic acid chloride.

One or two or more kinds of monocarbamoyl Cl bodies may be contained in the XDI composition.

As the details are described later, the monocarbamoyl Cl body is generated as a reaction intermediate of the XDI in the production of the XDI composition, and is generated by reaction of a hydrogen chloride with the XDI. A structural isomer of the generated monocarbamoyl Cl body corresponds to a structural isomer of the XDI as a raw material. For example, in the XDI composition, when the main component is the 1,3-XDI, the monocarbamoyl Cl body as a secondary component is the (3-(isocyanatomethyl)benzyl)carbamic acid chloride.

Of the monocarbamoyl Cl bodies, preferably, (3-(isocyanatomethyl)benzyl)carbamic acid chloride is used.

A content ratio of the monocarbamoyl Cl body is, for example, 1 ppm, preferably 10 ppm or more, more preferably 100 ppm or more, further more preferably 300 ppm or more, particularly preferably 1000 ppm or more, and for example, 10000 ppm or less, preferably 6000 ppm or less, more preferably 4000 ppm or less, further more preferably 2000 ppm or less with respect to the total mass of the XDI composition.

The content ratio of the monocarbamoyl Cl body is calculated from an amount of chlorine obtained by calculating a remaining amount of chlorine which excludes an amount of chlorine of a chlorine-containing component other than the monocarbamoyl Cl body (for example, DCI and CBI (described later)) from an amount of hydrolyzable chlorine (HC, described later) of the XDI composition. When the monocarbamoyl Cl body and the dicarbamoyl body are contained in the XDI composition, a ratio of the monocarbamoyl Cl body to the dicarbamoyl body is calculated by a difference in an inflection point confirmed when the XDI composition is titrated using an aqueous solution of alkali metal hydroxide. As the alkali metal hydroxide, a sodium hydroxide or a potassium hydroxide is used.

A mass ratio of the monocarbamoyl Cl body to the DCI is, for example, 1 or more, preferably 30 or more, more preferably 100 or more, further more preferably 200 or more, particularly preferably 400 or more, especially preferably 800 or more, and for example, 10000 or less, preferably 6000 or less, more preferably below 3000, further more preferably 1900 or less, particularly preferably 950 or less.

When the mass ratio of the monocarbamoyl Cl body to the DCI is the above-described lower limit or more, it is possible to stably improve heat resistance (glass transition temperature Tg) of the resin produced from the XDI composition. When the mass ratio of the monocarbamoyl Cl body to the DCI is the above-described upper limit or less, it is possible to sufficiently ensure the pot life when the XDI composition is mixed with an active hydrogen group-containing component to be described later. In particular, when the mass ratio of the monocarbamoyl Cl body to the DCI is below 3000, it is possible to improve releasability of the resin with respect to a mold when the resin is produced by casting method.

The DCI is the dichloromethylbenzyl isocyanate, and one isocyanatomethyl group of two isocyanatomethyl groups possessed by the XDI is substituted with a dichloromethyl group (—CHCl$_2$ group).

Examples of the DCI include 2-dichloromethylbenzyl isocyanate (o-DCI), 3-dichloromethylbenzyl isocyanate (m-DCI), and 4-dichloromethylbenzyl isocyanate (p-DCI).

One or two or more kinds of DCIs may be contained in the XDI composition.

As the details are described later, the DCI is secondarily produced in the production of the XDI. A structural isomer of the DCI which is secondarily produced corresponds to a structural isomer of the produced XDI. For example, in the XDI composition, when the main component is the 1,3-XDI, the DCI as a secondary component is the 3-dichloromethylbenzyl isocyanate.

Of the DCIs, preferably, 3-dichloromethylbenzyl isocyanate (m-DCI) is used.

A content ratio of the DCI is, for example, 0.1 ppm or more, preferably 0.6 ppm or more, and for example, 60 ppm or less, preferably 30 ppm or less, more preferably 10 ppm or less, further more preferably 5.0 ppm or less, particularly preferably 3.0 ppm or less, especially preferably below 2.0 ppm with respect to the total mass of the XDI composition. The content ratio of the DCI can be measured by analyzing with gas chromatography in conformity with the method described in Examples to be described later.

When the content ratio of DCI is the above-described upper limit or less, it is possible to further improve the heat resistance (glass transition temperature Tg) of the resin produced from the XDI composition.

Further, the XDI composition may contain a chloromethylbenzyl isocyanate represented by the following chemical formula (4). In the following, the chloromethylbenzyl isocyanate represented by the following chemical formula (4) is referred to as the CBI.

[Chemical Formula 3]

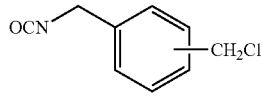

(4)

The CBI is a monochloromethylbenzyl isocyanate, and one isocyanatomethyl group of two isocyanatomethyl groups possessed by the XDI is substituted with a monochloromethyl group (—CH$_2$Cl group).

Examples of the CBI include 2-chloromethylbenzyl isocyanate (o-CBI), 3-chloromethylbenzyl isocyanate (m-CBI), and 4-dichloromethylbenzyl isocyanate (p-CBI).

One or two or more kinds of CBIs may be contained in the XDI composition.

As the details are described below, the CBI is secondarily produced in the production of the XDI. A structural isomer of the CBI which is secondarily produced corresponds to the structural isomer of the produced XDI. For example, in the XDI composition, when the main component is the 1,3-XDI, the CBI as a secondary component is the 3-chloromethylbenzyl isocyanate.

Of the CBIs, preferably, 3-chloromethylbenzyl isocyanate (m-CBI) is used.

A content ratio of the CBI is, for example, 0 ppm or more, preferably 0.2 ppm or more, more preferably 6 ppm or more, further more preferably 100 ppm or more, and for example, 5000 ppm or less, preferably 4000 ppm or less, more preferably 3000 ppm or less, further more preferably 1600 ppm or less, particularly preferably 1000 ppm or less with respect to the total mass of the XDI composition. The content ratio of the CBI can be measured in conformity with the method described in the [0376] and [0377] paragraphs of International Patent Publication No. WO2018/190290.

When the content ratio of the CBI is within the above-described range, it is possible to reliably improve yellowing resistance of the resin produced from the XDI composition. In particular, when the content ratio of the CBI is the above-described upper limit or less, it is possible to reliably improve the yellowing resistance of the resin produced from the XDI composition, and to improve mechanical properties of the resin.

The concentration of the hydrolyzable chlorine (HC) in the XDI composition is, for example, 0.15 ppm or more, preferably 1 ppm or more, more preferably 50 ppm or more, particularly preferably 100 ppm or more, and for example, 3000 ppm or less, preferably 2000 ppm or less, more preferably 1000 ppm or less. The concentration of the hydrolyzable chlorine (HC) is measured in conformity with the method for determining the hydrolyzable chlorine described in JIS K-1603-3 (2007).

The curing catalyst is preferably represented by the following chemical formula (3).

[Chemical Formula 4]

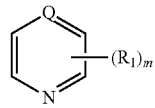

(3)

In the above-described chemical formula (3), $R_1$ represents a straight-chain alkyl group having 1 to 20 carbon atoms, a branched alkyl group having 3 to 20 carbon atoms, a cycloalkyl group having 3 to 20 carbon atoms, or a halogen atom.

Examples of the straight-chain alkyl group having 1 to 20 carbon atoms represented by $R_1$ include methyl group, ethyl group, n-propyl group, n-butyl group, pentyl group, hexyl group, heptyl group, n-octyl group, nonyl group, decyl group, and dodecyl group.

Examples of the branched alkyl group having 3 to 20 carbon atoms represented by $R_1$ include isopropyl group, isobutyl group, t-butyl group, isopentyl group, isooctyl group, 2-ethylhexyl group, 2-propylpentyl group, and isodecyl group.

Examples of the cycloalkyl group having 3 to 20 carbon atoms represented by $R_1$ include cyclopropyl group, cyclobutyl group, cyclopentyl group, cyclohexyl group, cycloheptyl group, and cyclooctyl group.

$R_1$ is preferably a straight-chain alkyl group having 1 to 20 carbon atoms, more preferably a straight-chain alkyl group having 1 to 4 carbon atoms, more preferably a methyl group.

In the above-described formula (3), "m" represents an integer of 0 to 5, preferably an integer of 0 to 3, more preferably 1 to 3. When "m" represents 2 to 5, the plurality of $R_1$s may be the same or different. Preferably, the plurality of $R_1$s are the same.

In the above-described chemical formula (3), Q represents a carbon atom or a nitrogen atom. Q is preferably a carbon atom.

Examples of the curing catalyst represented by the above-described chemical formula (3) include pyridine, 3-chloropyridine, 2-methylpyridine, 3-methylpyridine, 4-methylpyridine, 2-ethylpyridine, 3-ethylpyridine, 2,6-dimethylpyridine, 3,5-dimethylpyridine, 2,4,6-trimethylpyridine, and 2-methylpyrazine. As the curing catalyst, preferably, 3,5-dimethylpyridine and 2,4,6-trimethylpyridine are used.

A mole ratio of the curing catalyst to the monocarbamoyl Cl body represented by the chemical formula (1) is 2 or more, preferably 2.3 or more. When the mole ratio of the curing catalyst to the monocarbamoyl Cl body represented by the chemical formula (1) is the above-described lower limit value or more, it is possible to smoothly cure a polymerizable composition for an optical material.

The mole ratio of the curing catalyst to the monocarbamoyl Cl body represented by the chemical formula (1) is 4 or less, preferably 3 or less, more preferably 2.5 or less. When the mole ratio of the curing catalyst to the monocarbamoyl Cl body represented by the chemical formula (1) is the above-described upper limit value or less, it is possible to ensure the pot life of the polymerizable composition for an optical material.

The polymerizable composition for an optical material may contain a curing catalyst other than the above-described chemical formula (3).

Examples of the curing catalyst other than the chemical formula (3) include organic tin catalysts and Lewis acid catalysts.

Examples of the organic tin catalyst include dialkyltin halogenated compounds and dialkyltin dicarboxylate. Examples of the dialkyltin halogenated compound include dibutyltin dichloride and dimethyltin dichloride. Examples of the dialkyltin dicarboxylate include dimethyltin diacetate, dibutyltin dioctanoate, and dibutyltin dilaurate.

2. Method for Producing XDI Composition

Next, a method for producing an XDI composition is described.

In the production of the XDI composition, for example, a reaction mass is prepared by the method for producing an XDI composition described in the [0054] to [0110] paragraphs of International Patent Publication No. WO2018/190290, and then, the reaction mass is purified so that the content ratio of at least the XDI, the monocarbamoyl Cl body, and the DCI is within the above-described range.

In order to prepare the reaction mass, for example, a xylylene diamine and the hydrogen chloride are mixed, thereby forming a xylylene diamine hydrochloride salt, and then, the hydrochloride salt and a carbonyl chloride (phosgene) are reacted (phosgenation method of an amine hydrochloride salt).

In the following, the xylylene diamine is referred to as an XDA. Examples of the XDA include 1,2-XDA (o-XDA), 1,3-XDA (m-XDA), and 1,4-XDA (p-XDA), and preferably, 1,3-XDA (m-XDA) is used.

In a salt formation step of forming an XDA hydrochloride salt, for example, the XDA and the hydrogen chloride are mixed in the presence of an inert solvent, thereby producing (forming) the XDA hydrochloride salt.

Examples of the inert solvents include the inert solvent described in the [0059] paragraph of International Patent Publication No. WO2018/190290. These inert solvents may be used alone or in combination of two or more. Of the inert solvents, preferably, halogenated aromatic hydrocarbons are used, more preferably, chlorobenzene and dichlorobenzene are used.

Then, a hydrogen chloride gas is supplied to an amine solution in which the XDA is dissolved in the inert solvent. Thereafter, the hydrogen chloride gas and the amine solution are stirred and mixed.

A mass ratio (total amine concentration) of the XDA to the total sum of the mass of the XDA and the inert solvent is, for example, 3% by mass or more, preferably 5% by mass or more, and for example, 30% by mass or less, preferably 20% by mass or less, more preferably 15% by mass or less.

A supply ratio of the hydrogen chloride is, for example, 2 mol or more, and for example, 10 mol or less, preferably 6 mol or less, more preferably 4 mol or less with respect to 1 mol of the XDA.

A salt formation temperature in the salt formation step is, for example, 30° C. or more, preferably 50° C. or more, and for example, 160° C. or less, preferably 150° C. or less. A salt formation pressure (gauge pressure) in the salt formation step is, for example, the atmospheric pressure (0 MPaG) or more, preferably 0.01 MPaG or more, and for example, 1.0 MPaG or less, preferably 0.5 MPaG or less.

Thus, the XDA hydrochloride salt is generated from the XDA and the hydrogen chloride (hydrochlorination reaction), thereby producing a slurry containing the XDA hydrochloride salt.

Next, the carbonyl chloride is supplied to the slurry containing the XDA hydrochloride salt to react the XDA hydrochloride salt with the carbonyl chloride (isocyanate-formation reaction, phosgenation).

A supply ratio of the carbonyl chloride is, for example, 4 mol or more, preferably 5 mol or more, more preferably 6 mol or more, and for example, 50 mol or less, preferably 40 mol or less, more preferably 30 mol or less with respect to 1 mol of the XDA hydrochloride salt.

Reaction time of the isocyanate-formation step is, for example, 4 hours or more, preferably 6 hours or more, and for example, 25 hours or less, preferably 20 hours or less, more preferably 15 hours or less.

A reaction temperature in the isocyanate-formation step is, for example, 90° C. or more, preferably 100° C. or more, more preferably 110° C. or more, and for example, 190° C. or less, preferably 180° C. or less, more preferably 160° C. or less.

A reaction pressure (gauge pressure) in the isocyanate-formation step is, for example, above the atmospheric pressure (0 MPaG), preferably 0.0005 MPaG or more, more preferably 0.001 MPaG or more, further more preferably 0.003 MPaG or more, particularly preferably 0.01 MPaG (10 kPaG) or more, especially preferably 0.02 MPaG (20 kPaG) or more, most preferably 0.03 MPaG (30 kPaG) or more, and for example, 0.6 MPaG or less, preferably 0.4 MPaG or less, more preferably 0.2 MPaG or less.

The isocyanate-formation step is preferably carried out by continuous method. In other words, a slurry (XDA hydrochloride salt) generated in a stirring tank is continuously fed from the stirring tank into a reaction tank which is different from the stirring tank, and a reaction solution (reaction mass) is continuously taken out from the reaction tank, while the XDA hydrochloride salt and the carbonyl chloride are reacted in the reaction tank.

Thus, the XDA hydrochloride salt and the carbonyl chloride react, thereby generating the XDI as a main component. In addition, as a reaction intermediate of the XDI, a monocarbamoyl Cl body is generated.

Further, as described above, by excessively supplying the carbonyl chloride under pressurized conditions and carrying out the isocyanate-formation step of hydrochloride salt method by the continuous method, the CBI which is secondarily produced along with the production of the XDI, and chlorine which is inevitably contained in the carbonyl chloride react, thereby producing the DCI.

Then, if necessary, a degassing step, a desolvation step, and a tar-removing step are carried out with respect to a reaction solution (reaction mixture). In the degassing step, a gas such as the excessive carbonyl chloride and the hydrogen chloride which is secondarily produced is removed from the reaction solution (reaction mixture) with a known degassing column. In the desolvation step, an inert solvent is distilled off from the reaction solution with a known distillation column. In the tar-removing step, a tar component is removed from the reaction solution with a known tar-removing device.

As described above, the reaction mass containing at least the XDI, the monocarbamoyl Cl body, and the DCI is produced.

A content ratio of the XDI in the reaction mass is, for example, 80.0% by mass or more, preferably 90.0% by mass or more, more preferably 95.0% by mass or more, and for example, 99.0% by mass or less, preferably 98.5% by mass or less, more preferably 98.0% by mass or less.

A content ratio of the monocarbamoyl Cl body in the reaction mass is, for example, 5 ppm or more, preferably 10 ppm or more, more preferably 20 ppm or more, and for example, 10000 ppm or less, preferably 5000 ppm or less, more preferably 3000 ppm or less.

A content ratio of the DCI in the reaction mass is, for example, 1 ppm or more, preferably 2 ppm or more, more preferably 5 ppm or more, and for example, 80 ppm or less, preferably 70 ppm or less, more preferably 50 ppm or less.

The reaction mass can further contain the CBI. When the reaction mass contains the CBI, a content ratio of the CBI in the reaction mass is, for example, 0.1% by mass or more, preferably 0.3% by mass or more, more preferably 0.5% by mass or more, and for example, 3.0% by mass or less, preferably 1.5% by mass or less, more preferably 1.0% by mass or less.

Next, the reaction mass (composition before purification) is purified to adjust the respective content ratios of the monocarbamoyl Cl body and the DCI within the above-described range.

An example of a method for purifying the reaction mass includes distillation. In order to purify the reaction mass by distillation, for example, a low boiling material (low boiling point component) is distilled off from the reaction mass by distillation, and then, a low-boiling removed mass which is a reaction mass after low-boiling removing is rectified.

In the low-boiling removing step, for example, the reaction mass is distilled with a low-boiling removal column to distill off the low boiling material.

Examples of the low-boiling removal column include plate column and packed column, and preferably, packed column are used. A theoretical plate number of the low-boiling removal column is, for example, 3 plates or more, preferably 5 plates or more, more preferably 7 plates or more, and for example, 40 plates or less, preferably 20 plates or less, more preferably 15 plates or less.

A column bottom temperature of the low-boiling removal column is, for example, 130° C. or more, preferably 140° C. or more, more preferably 150° C. or more, and for example, 200° C. or less, preferably 190° C. or less, more preferably 180° C. or less.

A column top temperature of the low-boiling removal column is, for example, 90° C. or more, preferably 100° C. or more, more preferably 110° C. or more, and for example, 160° C. or less, preferably 150° C. or less, more preferably 140° C. or less.

A column top pressure of the low-boiling removal column is, for example, 0.05 kPa or more, preferably 0.1 kPa or more, more preferably 0.2 kPa or more, and for example, 3.0 kPa or less, preferably 2.0 kPa or less, more preferably 1.0 kPa or less.

A column top reflux ratio of the low-boiling removal column is, for example, 1 or more, preferably 5 or more, more preferably 10 or more, and for example, 80 or less, preferably 60 or less, more preferably 50 or less.

Retention time of the low-boiling removal column is, for example, 0.1 hours or more, preferably 0.2 hours or more, more preferably 0.3 hours or more, and for example, 10 hours or less, preferably 5 hours or less, more preferably 3 hours or less.

Thus, the low boiling material is distilled off, thereby obtaining the low-boiling removed mass as a can effluent.

Then, in the rectifying step, for example, the low-boiling removed mass is distilled with a rectifying column, and a fraction is taken out.

Examples of the rectifying column include plate column and packed column, and preferably, packed column are used. The theoretical plate number of the rectifying column is, for example, 1 plate or more, and for example, 20 plates or less, preferably 10 plates or less, more preferably 5 plates or less.

A column bottom temperature of the rectifying column is, for example, 120° C. or more, preferably 130° C. or more, more preferably 140° C. or more, and for example, 190° C. or less, preferably 180° C. or less, more preferably 170° C. or less.

A column top temperature of the rectifying column is, for example, 90° C. or more, preferably 110° C. or more, more preferably 130° C. or more, and for example, 180° C. or less, preferably 170° C. or less, more preferably 160° C. or less.

A column top pressure of the rectifying column is, for example, 0.05 kPa or more, preferably 0.1 kPa or more, more preferably 0.2 kPa or more, and for example, 3.0 kPa or less, preferably 2.0 kPa or less, more preferably 1.0 kPa or less.

A column top reflux ratio of the rectifying column is, for example, 0.1 or more, preferably 0.2 or more, more preferably 0.3 or more, and for example, 50 or less, preferably 20 or less, more preferably 10 or less.

Retention time of the rectifying column is, for example, 0.2 hours or more, preferably 0.5 hours or more, more preferably 1.0 hour or more, and for example, 20 hours or less, preferably 10 hours or less.

As described above, the XDI composition is taken out as a fraction, and in the XDI composition, the content ratio of the XDI, the monocarbamoyl Cl body, and the DCI can be adjusted within the above-described range. It is also possible to adjust the content ratio of the DCI in the XDI composition by adding the DCI to the XDI composition after the rectifying. Further, it is also possible to supply a hydrogen chloride gas to the XDI composition after the rectifying to adjust the content ratio of the monocarbamoyl Cl body in the XDI composition.

As in Examples to be described later, experimentally, it is also possible to prepare an XDI composition containing the XDI and the DCI, and containing substantially no monocarbamoyl Cl body (no MCC body containing XDI composition), and to supply a hydrogen chloride gas to the no MCC body containing XDI composition, thereby producing an XDI composition containing the XDI, the monocarbamoyl Cl body, and the DCI at the above-described ratio.

To prepare the no MCC body containing XDI composition, for example, in the low-boiling removing step and the rectifying step, the monocarbamoyl Cl body contained in the reaction mass is thermally decomposed to be converted into the XDI. In the no MCC body containing XDI composition, a content ratio of the monocarbamoyl Cl body is, for example, below 0.05 ppm, preferably 0 ppm.

Next, the hydrogen chloride gas is supplied to the no MCC body containing XDI composition at normal temperature (25° C.) under normal pressure (0.1 MPa).

A supply amount of the hydrogen chloride is, for example, 0.08 mmol or more, and for example, 10 mmol or less, preferably 8.0 mmol or less, more preferably 6.0 mmol or less with respect to 1 mol of the XDI in the no MCC body containing XDI composition.

When the supply amount of the hydrogen chloride is the above-described upper limit value or less, mainly the XDI reacts with the hydrogen chloride, thereby generating a monocarbamoyl Cl body almost quantitatively from the supplied hydrogen chloride. The DCI and the CBI are present in trace amounts with respect to the XDI. Therefore, it is considered extremely unlikely that the isocyanato groups of the DCI and the CBI react with the hydrogen chloride to generate the carbamoyl Cl body. Therefore, by adjusting the supply amount of the hydrogen chloride, it is possible to adjust the content ratio of the monocarbamoyl Cl body in the XDI composition. The content ratio of the monocarbamoyl Cl body in the XDI composition is measured by the above-described measurement method.

<Function and Effect>

The above-described XDI composition contains the XDI, the monocarbamoyl Cl body represented by the above-described chemical formula (1), and the DCI represented by the above-described chemical formula (2). Therefore, the resin produced from the above-described XDI composition has excellent heat resistance.

Further, the mass ratio of the monocarbamoyl Cl body to the DCI is preferably below 3000. However, the resin may be produced by being molded into a desired shape by known casting method. In this case, when the mass ratio of the monocarbamoyl Cl body to the DCI in the above-described XDI composition is below 3000, it is possible to improve the releasability of the resin with respect to the mold, and to suppress damage to the resin when the resin is removed from the mold.

3. Polymerizable Composition

The above-described XDI composition is used as a raw material for a resin, and in particular, is preferably used as a raw material for an optical material. In other words, the XDI composition is preferably contained in the polymerizable composition for an optical material as an isocyanate component.

The polymerizable composition for an optical material contains an isocyanate component and an active hydrogen group-containing component.

The isocyanate component contains the XDI composition, and preferably consists of the XDI composition.

Examples of the active hydrogen group-containing component include polyol components, polythiol components, and polyamine components.

These active hydrogen group-containing components may be used alone or in combination of two or more.

Of the active hydrogen group-containing components, for example, from the viewpoint of optical properties, preferably, polythiol components are used.

Examples of the polythiol component include aliphatic polythiol compounds, aromatic polythiol compounds, and heterocyclic polythiol compounds.

Examples of the aliphatic polythiol compound include methane dithiol, 1,2-ethanedithiol, 1,2,3-propanetrithiol, 1,2-cyclohexanedithiol, bis(2-mercaptoethyl)ether, tetrakis (mercaptomethyl)methane, diethylene glycolbis(2-mercapto acetate), diethylene glycolbis(3-mercaptopropionate), ethylene glycolbis(2-mercaptoacetate), ethylene glycolbis(3-mercaptopropionate), trimethylolpropane tris(2-mercapto acetate), trimethylolpropane tris(3-mercaptopropionate), trimethylolethane tris(2-mercapto acetate), trimethylolethane tris(3-mercaptopropionate), pentaerythritol tetrakis(2-mercaptoacetate), pentaerythritol tetrakis(3-mercaptopropionate), bis(mercaptomethyl)sulfide, bis(mercaptomethyl) disulfide, bis(mercapto ethyl)sulfide, bis(mercapto ethyl) disulfide, bis(mercaptopropyl)sulfide, bis(mercaptomethylthio)methane, bis(2-mercaptoethylthio) methane, bis(3-mercaptopropylthio)methane, 1,2-bis (mercaptomethylthio)ethane, 1,2-bis(2-mercaptoethylthio) ethane, 1,2-bis(3-mercaptopropylthio)ethane, 1,2,3-tris (mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8- dimercaptomethyl-1,11-dimercapto-3,6,9-trithiaundecane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane, and esters of these thioglycolic acids and mercaptopropionic acids, hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercaptopropionate), thiodiglycol acid bis(2-mercaptoethyl ester), thiodipropion acid bis(2-mercaptoethyl ester), dithiodiglycol acid bis(2-mercaptoethyl ester), dithiodipropion acid bis(2-mercaptoethyl ester), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptomethylthio)ethyl)-1,3-dithiethane, 3-mercaptomethyl-1,5-dimercapto-2,4-dithiapentane, tris(mercaptomethylthio)methane, tris(mercaptoethylthio)methane, and 2,5-bis(mercaptomethyl)-1,4-dithiane.

Examples of the aromatic polythiol compound include 1,2-dimercaptobenzene, 1,3-dimercaptobenzene, 1,4-dimethylcaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,3,5-trimercaptobenzene, 1,3,5-tris(mercaptomethyl)benzene, 1,3,5-tris(mercaptomethyleneoxy)benzene, 1,3,5-tris(mercaptoethyleneoxy)benzene, 2,5-toluenedithiol, 3,4-toluenedithiol, 1,5-naphthalenedithiol, and 2,6-naphthalenedithiol.

Examples of the heterocyclic polythiol compound include 2-methylamino-4,6-dithiol-sym-triazine, 3,4-thiophenedithiol, and bismuthiol.

These polythiol components may be used alone or in combination of two or more.

As the polythiol component, preferably at least one kind selected from the group consisting of 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, 2-(2,2-bis(mercaptomethylthio)ethyl)-1,3-dithiethane, 1,1,2,2-tetrakis(mercaptomethylthio)ethane, 3-mercaptomethyl-1,5-dimercapto-2,4-dithiapentane, tris(mercaptomethylthio)methane, ethylene glycol bis(3-mercaptopropionate), and diethylene glycol bis(3-mercaptopropionate) is used.

3. Resin

By reacting the above-described isocyanate component with the above-described active hydrogen group-containing component, the resin is produced. In other words, the resin is a cured product of the polymerizable composition for an optical material. Therefore, the resin is an optical material. The resin is preferably molded by known molding method. In other words, a molded article contains the resin. Therefore, the molded article is the optical component. Examples of the molded article of the resin include optical elements.

Examples of the optical element include lens, sheet, and film, and preferably, lens is used.

The lens is produced, for example, by reaction of the above-described XDI composition with the above-described polythiol component. For example, casting method may be used in the production of the lens.

Examples of the lens include transparent lens, sunglass lens, polarized lens, spectacle lens, camera lens, pick-up lens, and contact lens.

<Function and Effect>

The resin, the molded article, the optical element, and the lens described above contain the cured product of the polymerizable composition for an optical material described above. Therefore, the resin, the molded article, the optical element, and the lens have excellent heat resistance.

The above-described XDI composition can be also used as a raw material for coating (for example, paint and adhesive). In this case, the XDI composition is modified by known method if necessary, and is contained as an isocyanate component in the polymerizable composition for coating.

A xylylene diisocyanate modified composition (hereinafter, referred to as an XDI modified composition) is produced by modifying the above-described XDI composition, and contains at least one kind of functional groups of the following (a) to (i):

(a) isocyanurate group
(b) allophanate group
(c) biuret group
(d) urethane group
(e) urea group
(f) iminooxadiazinedione group
(g) uretdione group
(h) uretonimine group
(i) carbodiimide group More specifically, the XDI modified composition containing the functional group of the above-described (a) (isocyanurate group) contains a trimer of the XDI, and can be obtained, for example, by adding a known isocyanuration catalyst to an XDI monomer composition to be reacted, and subjecting the XDI to isocyanuration (for example, trimerization) of the XDI.

The XDI modified composition containing the functional group of the above-described (b) (allophanate group) contains an allophanate modified product of the XDI, and can be obtained, for example, by reacting the XDI monomer composition with a monohydric alcohol or a dihydric alcohol, and then, adding a known allophanatization catalyst to be further reacted.

The XDI modified composition containing the functional group of the above-described (c) (biuret group) contains a biuret modified product of the XDI, and can be obtained, for example, by reacting the XDI monomer composition with water or a secondary amine, and then, adding a known biuret-forming catalyst to be further reacted.

The XDI modified composition containing the functional group of the above-described (d) (urethane group) contains a polyol modified product of the XDI, and can be obtained, for example, by reaction of the XDI monomer composition with a low molecular weight polyol (for example, trimethylolpropane).

The XDI modified composition containing the functional group of the above-described (e) (urea group) contains a polyamine modified product of the XDI, and can be obtained, for example, by reaction of the XDI composition with a polyamine.

The XDI modified composition containing the functional group of the above-described (f) (iminooxadiazinedione group) contains an iminooxadiazinedione modified product (asymmetric trimer) of the XDI, and can be obtained, for example, by reacting the XDI composition in the presence of a known iminooxadiazinedionization catalyst and subjecting the XDI to iminooxadiazinedionization (for example, trimerization).

The XDI modified composition containing the functional group of the above-described (g) (uretdione group) contains a uretdione modified product of the XDI, and can be obtained, for example, by a method of applying heat to the XDI composition at around 90° C. to 200° C., or reacting the XDI composition in the presence of a known uretdionization catalyst and subjecting the XDI to uretdionization (for example, dimerization).

The XDI modified composition containing the functional group of the above-described (h) (uretonimine group) contains a uretonimine modified product of the XDI, and can be obtained, for example, by reacting the XDI composition in the presence of a known carbodiimidation catalyst to form a carbodiimide group, and then, adding the XDI to the carbodiimide group.

The XDI modified composition containing the functional group of the above-described (i) (carbodiimide group) contains a carbodiimide modified product of the XDI, and can be obtained, for example, by reacting the XDI composition in the presence of a known carbodiimidation catalyst.

The XDI modified composition may contain at least one kind of functional groups of the above-described (a) to (i), or may contain two or more kinds of them. These XDI modified compositions may be used alone or in combination of two or more.

The polymerizable composition for coating is, for example, a two-component curable resin raw material, and contains an A agent as a curing agent and a B agent as a main agent.

The A agent contains, for example, the above-described XDI modified composition. The B agent contains, for example, a polyol component.

The coating formed from the polymerizable composition for coating has also excellent heat resistance.

EXAMPLES

Next, the present invention is further described based on Examples below. The present invention is however not limited by these Examples. The specific numerical values in mixing ratio (content ratio), property value, and parameter used in the following description can be replaced with upper limit values (numerical values defined as "or less" or "below") or lower limit values (numerical values defined as "or more" or "above") of corresponding numerical values in mixing ratio (content ratio), property value, and parameter described in the above-described "DESCRIPTION OF EMBODIMENTS". All designations of "part" or "parts" and "%" mean part or parts by mass and % by mass, respectively, unless otherwise particularly specified.

<Measurement Method>

A method for measuring the content ratio of the compound (DCI) represented by the above-described chemical formula (2) and a method for measuring the pot life are as follows.

<<Content Ratio of DCI>>

The DCI having purity of 99 mol % synthesized in the same manner as in Preparation Example 1 of International Patent Publication No. WO2018/190290 was used as a standard material, and analyzed by gas chromatography under the following conditions, thereby preparing a calibration curve from an area value of the obtained gas chromatogram (absolute calibration curve method).

Next, each of the XDI compositions of Examples to be described later was analyzed by gas chromatography under the following conditions, thereby obtaining the number of moles of the DCI. The obtained number of moles of the DCI was converted into mass, thereby calculating the content ratio of the DCI in each of the XDI compositions of Examples to be described later. Retention time of the DCI was 16.6 minutes.

Device: HP-6890/5873 (manufactured by Hewlett-Packard Company)

Column: HP-50+, inner diameter of 0.25 mmx length of 30 mx film thickness of 0.25 μm (manufactured by Hewlett-Packard Company)

Oven temperature: temperature rising from 50° C. to 280° C. at 10° C./min, and held for six minutes after reaching 280° C.

Split ratio: pulsed splitless method
Injection port temperature: 200° C.
Detector temperature: 280° C.
Carrier gas: He
Carrier gas flow rate: 1.0 ml/min (constant flow control)
Sample concentration: 1.0% by mass dichloromethane solution
Injection amount: 1.0 μL
Detection method: SIM (monitoring ion: m/z, 180, 215)

<<Pot Life>>

Each of the XDI compositions obtained in Examples (50.8 parts by mass) and 0.01 parts by mass of a dimethyltin dichloride as a curing catalyst were mixed and dissolved at 20° C. Subsequently, 49.2 parts by mass of a polythiol component containing 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane as a main component was charged and mixed, thereby obtaining a mixed uniform solution. The obtained mixed uniform solution (10 g) was charged into a sample bottle and stirred with a magnetic stirrer under a temperature condition of 25° C. The stirring state was visually confirmed every one hour, and the time of a state in which the viscosity of the mixed uniform solution increased, and the stirring with the magnetic stirrer became impossible was measured. It was judged that the longer the time, the more excellent the pot life.

Preparation Example: Preparation of XDI Composition Containing Substantially No Monocarbamoyl Cl Body (No MCC Body Containing XDI Composition)

Preparation Example 1

A no MCC body containing XDI composition was produced in conformity with the method described in International Patent Publication No. WO2018/190290.

Specifically, a stirring tank was charged with 457.5 parts by mass of an orthodichlorobenzene (ODCB) and 43 parts by mass of an m-XDA (total amine concentration of 9% by mass). Next, after raising a temperature thereof to 120° C., a hydrogen chloride gas was blown into a liquid mixture of the ODCB and the XDA at a rate of 23 parts by mass/hr for two hours. Thus, a slurry containing a hydrochloride salt of the XDA was obtained.

Then, the slurry (XDA hydrochloride salt) was continuously fed from the stirring tank into a reaction tank which was different from the stirring tank, and a reaction mass was continuously taken out from the reaction tank, while the carbonyl chloride was supplied to the XDA hydrochloride salt to be reacted in the reaction tank.

A reaction temperature of the hydrochloride salt of the XDA with the carbonyl chloride was 150° C., and a reaction pressure (gauge pressure) of the hydrochloride salt of the XDA with the carbonyl chloride was 0.03 MPaG In addition, a supply ratio of the carbonyl chloride to 1 mol of the hydrochloride salt of the XDA was 12 mol.

Next, the reaction mass was degassed and then, desolvated, and further a tar component was removed therefrom.

Thereafter, the reaction mass from which the tar component was removed was distilled in a low-boiling removal column under the following conditions, thereby removing a low boiling material. The low-boiling removal column was filled with a filling material corresponding to the ten plates in a theoretical plate number.

Low-boiling Removing Conditions in Low-boiling Removal Column:
Column bottom temperature: 160 to 170° C.
Column top temperature: 115 to 125° C.
Column top pressure: 0.5 to 1.0 kPa
Column top reflux rate: 100 parts/hr
Distilling amount of low boiling material: 3.1 parts/hr
Column top reflux ratio: 32
Retention time: 0.3 to 3 hr Next, the reaction mass from which the low boiling material was removed was rectified with a rectifying column under the following conditions, thereby obtaining an XDI composition as a fraction. The rectifying column was filled with a filling material corresponding to the three plates in the theoretical plate number.

Rectifying Conditions in Rectifying Column:
Column bottom temperature: 150 to 160° C.
Column top temperature: 140 to 150° C.
Column top pressure: 0.5 to 0.8 kPa
Distilling Amount of XDI Composition: 93.7 parts/hr
Column top reflux ratio: 1
Retention time: 1 to 10 hr As described above, the no MCC body containing XDI composition was produced.

Preparation Example 2

A no MCC body containing XDI composition was produced in the same manner as in Preparation Example 1. In Preparation Example 2, the reaction pressure (gauge pressure) of the hydrochloride salt of the XDA and the carbonyl chloride was changed to 0.044 MPaG, and the supply ratio of the carbonyl chloride to 1 mol of the hydrochloride salt of the XDA was changed to 13.0 mol. Further, the distilling amount of the low boiling material in the low-boiling removal column was changed to 3.4 parts/hr, and the column top reflux ratio was changed to 29. Further, the distilling amount of the XDI composition in the rectifying column was changed to 93.8 parts/hr.

Preparation Example 3

A no MCC body containing XDI composition was produced in the same manner as in Preparation Example 2. In Preparation Example 3, the reaction pressure (gauge pressure) of the hydrochloride salt of the XDA and the carbonyl chloride was changed to 0.07 MPaG, and the supply ratio of the carbonyl chloride to 1 mol of the hydrochloride salt of the XDA was changed to 15.2 mol.

Examples 1 to 24: Preparation of XDI Composition

A hydrogen chloride gas was blown into each of the no MCC body containing XDI compositions immediately after the rectifying obtained in Preparation Examples so that the content ratio of the monocarbamoyl Cl body in the XDI composition was a target value. Thus, an XDI composition was obtained.

A content ratio of the monocarbamoyl Cl body in the obtained XDI composition was measured by the above-described measurement method. The results are shown in Table 1.

Further, a content ratio of the DCI in each of the XDI compositions was measured in accordance with the above-described measurement method. The results are shown in Table 1. In addition, a mass ratio of the monocarbamoyl Cl body to the DCI is shown in Table 1.

Also, the pot life when each of the XDI compositions was mixed with the polythiol component was measured in accordance with the above-described measurement method. The results are shown in Table 1.

Further, the pot life of the polymerizable composition for an optical material was measured in accordance with the following measurement method. The results are shown in Table 2. In addition, a mole ratio of the catalyst to the monocarbamoyl Cl body is shown in Table 2.

<<Pot Life>>

The curing catalyst shown in Table 2 was mixed and dissolved in 50.8 parts by mass of the XDI composition of Example 1 at 20° C. at a mixing amount shown in Table 2. Subsequently, 49.2 parts by mass of a polythiol component containing 4,8-dimercaptomethyl-1,11-dimercapto-3,6,9-trithiaundecane, 4,7-dimercaptomethyl-1,11-dimercapto-3,6,9-trithiaundecane, and 5,7-dimercaptomethyl-1,11-dimercapto-3,6,9-trithiaundecane as a main component was charged and mixed, thereby obtaining each of the polymerizable compositions for an optical material of Examples 25 to 27 and Comparative Examples 1 to 4 as a mixed uniform solution. The obtained each of the polymerizable compositions for an optical material was charged into a sample bottle and stirred with a magnetic stirrer under a temperature condition of 20° C.

The viscosity (mPa·s) at 20° C. of the polymerizable composition for an optical material was measured every one hour using a B-type viscometer manufactured by Brookfield.

The time when the viscosity (mPa·s) at 20° C. of the polymerizable composition for an optical material was above 40 mPa·s was defined as the time (A), and the time when the viscosity (mPa·s) at 20° C. thereof was above 1000 mPa·s was defined as the time (B).

<Production of Plastic Lens>

Each of the XDI compositions obtained in Examples (50.2 parts by mass), 0.01 parts by mass of a dimethyltin dichloride as a curing catalyst, 0.10 parts by mass of ZELEC UN (trade name, manufactured by Stepan Company, acid phosphate ester), and 1.5 parts by mass of BioSorb 583 (manufactured by KYODO CHEMICAL CO., LTD., ultraviolet absorber) were mixed and dissolved at 20° C. Then, 49.2 parts by mass of a polythiol composition containing 4,8-dimercaptomethyl-1,11-dimercapto-3,6,9-trithiandecane, 4,7-dimercaptomethyl-1,11-dimercapto-3,6,9-trithiandecane, and 5,7-dimercaptomethyl-1,11-dimercapto-3,6,9-trithiandecane as a main component was charged and mixed into the obtained liquid mixture, thereby obtaining a uniform solution.

The uniform solution was defoamed at 600 Pa for one hour, and thereafter, filtration was carried out with a 1-μm Teflon (trademark) filter to be then injected into a mold consisting of a glass mold and a tape. The mold was put into an oven, and the temperature thereof was gradually increased from 25° C. to 120° C. to be polymerized for 24 hours. After completion of the polymerization, the mold was taken out from the oven, and the mold was removed to obtain a resin (plastic lens). The resin had a disc shape having a thickness of 9 mm and a diameter of 75 mm.

Further, the releasability of the resin was evaluated based on the following criteria. The results are shown in Table 1.

A: When the resin was released from the glass mold, both the glass mold and the resin could be released without breaking.

B: When the resin was released from the glass mold, the glass mold did not break, but the resin was broken.

C: After the heat polymerization and cooling, when the resin was released from the glass mold, the glass mold was already broken.

Thereafter, the obtained resin was further annealed at 120° C. for one hour, thereby producing a plastic lens.

Figure 2:
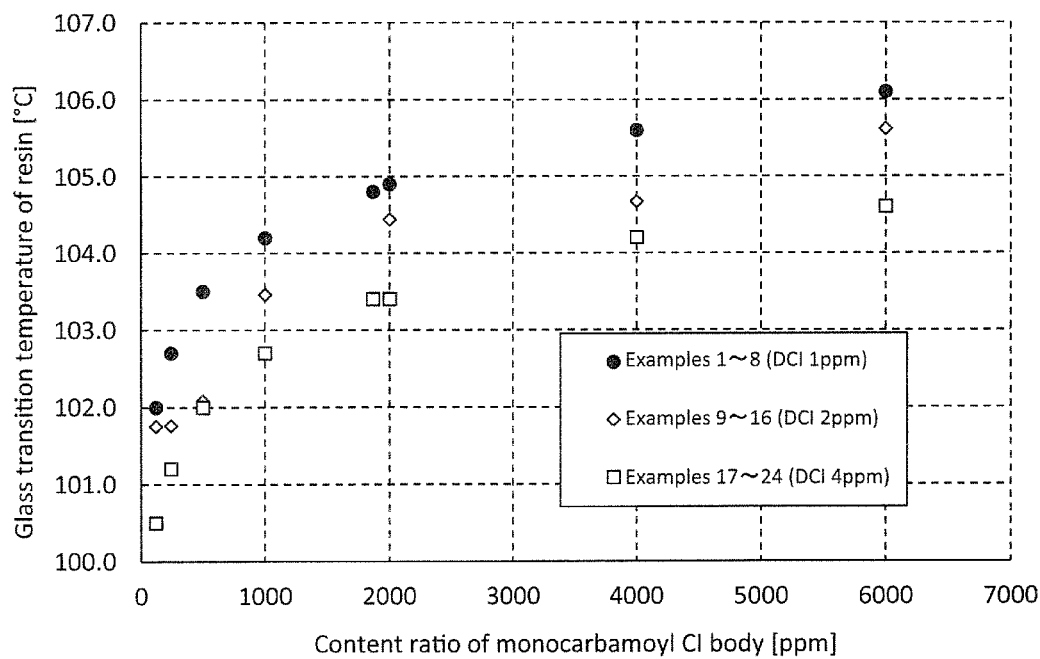
FIG. 2 shows a graph illustrating the correlation between a content ratio of an isocyanatomethylbenzyl carbamic acid chloride in each xylylene diisocyanate composition of Examples and a glass transition temperature of a resin.

Then, the glass transition temperature Tg of the obtained plastic lens was measured by TMA penetration method (load of 50 g, pin tip of 0.5 mmφ, temperature rising rate of 10° C./min) using a thermomechanical analyzer TMA-60 manufactured by Shimazu Corporation to be used as an index of heat resistance. The results are shown in Table 1. Further, the correlation between the mass ratio of the monocarbamoyl Cl body to the DCI in each of the XDI compositions of Examples, and the glass transition temperature (Tg) of the resin (plastic lens) is shown in FIG. 1. Further, the correlation between the content ratio of the monocarbamoyl Cl body in each of the XDI compositions of Examples, and the glass transition temperature (Tg) of the resin (plastic lens) is shown in FIG. 2.

TABLE 1

| No. | | Ex. 1 | Ex. 2 | Ex. 3 | Ex. 4 | Ex. 5 | Ex. 6 | Ex. 7 | Ex. 8 |
|---|---|---|---|---|---|---|---|---|---|
| no MCC Body containing XDI Composition | | | | | Preparation Ex. 1 | | | | |
| Content Ratio of Monocarbamoyl CI Body in XDI Composition [ppm] | | 122 | 243 | 501 | 1001 | 1867 | 2000 | 4000 | 6000 |
| Content Ratio of DCI in XDI Composition [ppm] | | 1 | 1 | 1 | 1 | 1 | 1 | 1 | 1 |
| Monocarbamoyl CI Body/DCI | | 122 | 243 | 501 | 1001 | 1867 | 2000 | 4000 | 6000 |
| Pot Life [hr] | | 3 | 3 | 3 | 3 | 3 | 2 | 2 | 1 |
| Resin Properties | Heat Resistance Tg [° C.] | 102.0 | 102.7 | 103.5 | 104.2 | 104.8 | 104.9 | 105.6 | 106.1 |
| | Releasability | A | A | A | B | B | B | C | C |

| No. | | Ex. 9 | Ex. 10 | Ex. 11 | Ex. 12 | Ex. 13 | Ex. 14 | Ex. 15 | Ex. 16 |
|---|---|---|---|---|---|---|---|---|---|
| no MCC Body containing XDI Composition | | | | | Preparation Ex. 2 | | | | |
| Content Ratio of Monocarbamoyl CI Body in XDI Composition [ppm] | | 122 | 243 | 501 | 1001 | 1867 | 2000 | 4000 | 6000 |
| Content Ratio of DCI in XDI Composition [ppm] | | 2 | 2 | 2 | 2 | 2 | 2 | 2 | 2 |
| Monocarbamoyl CI Body/DCI | | 61 | 122 | 251 | 501 | 934 | 1000 | 2000 | 3000 |
| Pot Life [hr] | | 5 | 3 | 3 | 3 | 3 | 3 | 2 | — |
| Resin Properties | Heat Resistance Tg [° C.] | 101.8 | 101.8 | 102.1 | 103.5 | — | 104.4 | 104.7 | 105.6 |
| | Releasability | A | A | A | A | — | B | B | C |

| No. | | Ex. 17 | Ex. 18 | Ex. 19 | Ex. 20 | Ex. 21 | Ex. 22 | Ex. 23 | Ex. 24 |
|---|---|---|---|---|---|---|---|---|---|
| no MCC Body containing XDI Composition | | | | | Preparation Ex. 3 | | | | |
| Content Ratio of Monocarbamoyl CI Body in XDI Composition [ppm] | | 122 | 243 | 501 | 1001 | 1867 | 2000 | 4000 | 6000 |
| Content Ratio of DCI in XDI Composition [ppm] | | 4 | 4 | 4 | 4 | 4 | 4 | 4 | 4 |
| Monocarbamoyl CI Body/DCI | | 31 | 61 | 125 | 250 | 467 | 500 | 1000 | 1500 |
| Pot Life [hr] | | 5 | 5 | 3 | 3 | 3 | 3 | 3 | — |
| Resin Properties | Heat Resistance Tg [° C.] | 100.5 | 101.2 | 102.0 | 102.7 | 103.4 | 103.4 | 104.2 | 104.6 |
| | Releasability | A | A | A | A | A | A | B | B |

TABLE 2

|  | Ex. 25 | Ex. 26 | Ex. 27 | Ex. 28 | Ex. 29 | Comparative Ex. 1 | Comparative Ex. 2 |
| --- | --- | --- | --- | --- | --- | --- | --- |
| XDI Composition (parts by mass) | 50.8 | 50.8 | 50.8 | 50.8 | 50.8 | 50.8 | 50.8 |
| Amount of Monocarbamoyl Cl Body in XDI Composition (ppm) | 122 | 122 | 122 | 122 | 122 | 122 | 122 |
| Curing Catalyst 3,5-dimethylpyridine (parts by mass) | 0.0093 | 0.0220 |  |  |  | 0.0050 |  |
| 2,4,6-trimethylpyridine |  |  | 0.0080 | 0.0120 | 0.0167 |  | 0.0060 |
| Mole Ratio of Curing Catalyst to Monocarbamoyl Cl Body | 3.15 | 7.44 | 2.39 | 3.59 | 5.00 | 1.69 | 1.80 |
| Polythiol Component (parts by mass) | 49.2 | 49.2 | 49.2 | 49.2 | 49.2 | 49.2 | 49.2 |
| Pot Life Time (A) | 2.5 | below 1 | 5.5 | 2.5 | below 1 | above 21 | 21 |
| Time (B) | 21 | 2 | 21 | 6.5 | 3.5 | above 21 | above 21 |

According to the results shown in Table 2, the time (A) of Comparative Example 1 is longer than the time (B) of Examples 25 and 26. Therefore, it can be judged that thermal curing in the polymerizable composition for an optical material of Comparative Example 1 is harder to proceed than that in each of the polymerizable compositions for an optical material of Examples 25 and 26.

The time (A) of Comparative Example 2 is longer than the time (B) of Examples 27, 28, and 29. Therefore, it can be judged that thermal curing in the polymerizable composition for an optical material of Comparative Example 2 is harder to proceed than that in each of the polymerizable compositions for an optical material of Examples 27, 28, and 29.

The invention claimed is:

1. A xylylene diisocyanate composition comprising:
a xylylene diisocyanate, a compound represented by the following chemical formula (1), and a compound represented by the following chemical formula (2)

[Chemical Formula 1]

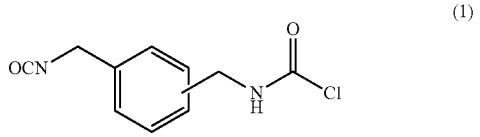

(1)

[Chemical Formula 2]

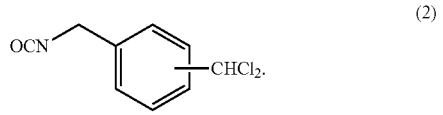

(2)

2. The xylylene diisocyanate composition according to claim 1, wherein
a mass ratio of the compound represented by the chemical formula (1) to the compound represented by the chemical formula (2) is 10000 or less.

3. The xylylene diisocyanate composition according to claim 2, wherein
a mass ratio of the compound represented by the chemical formula (1) to the compound represented by the chemical formula (2) is below 3000.

4. The xylylene diisocyanate composition according to claim 1, further comprising:
a curing catalyst represented by the following chemical formula (3), wherein
a mole ratio of the curing catalyst to the compound represented by the chemical formula (1) is 2 or more

[Chemical Formula 3]

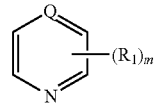

(3)

in chemical formula (3), $R_1$ represents a straight-chain alkyl group having 1 to 20 carbon atoms, a branched alkyl group having 3 to 20 carbon atoms, a cycloalkyl group having 3 to 20 carbon atoms, or a halogen atom; "m" represents an integer of 0 to 5; when "m" is 2 to 5, the plurality of $R_1$s may be the same or different; Q represents a carbon atom or a nitrogen atom.

5. The xylylene diisocyanate composition according to claim 4, wherein
the curing catalyst is at least one kind selected from pyridine, 3-chloropyridine, 2-methylpyridine, 3-methylpyridine, 4-methylpyridine, 2-ethylpyridine, 3-ethylpyridine, 2,6-dimethylpyridine, 3,5-dimethylpyridine, 2,4,6-trimethylpyridine, and 2-methylpyrazine.

6. A polymerizable composition for an optical material comprising: the xylylene diisocyanate composition according to claim 1 and an active hydrogen group-containing component.

7. The polymerizable composition for an optical material according to claim 6, wherein
the active hydrogen-containing component includes at least one kind of polythiol selected from the group consisting of 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 4-mercaptomethyl-1,8-dimercapto-3,6-dithiaoctane, pentaerythritol tetrakis(2-mercaptoacetate), pentaerythritol tetrakis(3-mercaptopropionate), 2,5-bis(mercaptomethyl)-1,4-dithiane, bis(mercaptoethyl)sulfide, 1,1,3,3-tetrakis(mercaptomethylthio)propane, 4,6-bis(mercaptomethylthio)-1,3-dithiane, bis(mercaptomethylthio)ethyl)-1,3-dithiethane, 1,1,2,2-tetrakis(mercaptomethylthio)ethane, 3-mercaptomethyl-1,5-dimercapto-2,4-dithiapentane, tris(mercaptomethylthio)methane, and ethylene glycol bis(3-mercaptopropionate).

8. A resin being a cured product of the polymerizable composition for an optical material according to claim 6.

9. A molded article comprising:
the resin according to claim 8.
10. An optical element comprising:
the molded article according to claim 9.
11. A lens comprising:
the optical element according to claim 10.

* * * * *

UNITED STATES PATENT AND TRADEMARK OFFICE
CERTIFICATE OF CORRECTION

| | |
|---|---|
| PATENT NO. | : 11,753,367 B2 |
| APPLICATION NO. | : 17/999678 |
| DATED | : September 12, 2023 |
| INVENTOR(S) | : Masayuki Takaguchi and Masaru Kawaguchi |

It is certified that error appears in the above-identified patent and that said Letters Patent is hereby corrected as shown below:

In the Claims

In Column 22, Lines 60-61:
"bis(mercaptomethylthio)ethyl)-1,3-dithiethane"
Should read:
-- 2-(2,2-bis(mercaptomethylthio)ethyl)-1,3-dithiethane --.

Signed and Sealed this
Seventh Day of November, 2023

Katherine Kelly Vidal
*Director of the United States Patent and Trademark Office*